(12) United States Patent
Henningsen et al.

(10) Patent No.: US 8,399,596 B2
(45) Date of Patent: Mar. 19, 2013

(54) EPOXY RESIN COMPOSITIONS AND PROCESS FOR PREPARING THEM

(75) Inventors: Michael Henningsen, Frankenthal (DE); Lars Wittenbecher, Duesseldorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 458 days.

(21) Appl. No.: 12/518,175

(22) PCT Filed: Nov. 30, 2007

(86) PCT No.: PCT/EP2007/063100
§ 371 (c)(1),
(2), (4) Date: Dec. 17, 2009

(87) PCT Pub. No.: WO2008/068205
PCT Pub. Date: Jun. 12, 2008

(65) Prior Publication Data
US 2010/0105856 A1    Apr. 29, 2010

(30) Foreign Application Priority Data
Dec. 7, 2006   (EP) ...................................... 06125591

(51) Int. Cl.
*C08G 59/00*   (2006.01)
(52) U.S. Cl. .......................................... 528/87; 528/86
(58) Field of Classification Search ...................... 528/87
See application file for complete search history.

(56) References Cited

U.S. PATENT DOCUMENTS 3,551,517 A * 12/1970 Dowbenko et al. ............ 525/110
5,162,547 A   11/1992 Roth et al.
5,668,227 A *  9/1997 Wolleb et al. .................. 525/507
2003/0098649 A1   5/2003 Murai et al.
2006/0025626 A1*  2/2006 Kohlstruk et al. ............ 560/338
2007/0149793 A1   6/2007 Arndt et al.

FOREIGN PATENT DOCUMENTS

| DE | 10 2005 003 116 | 7/2006 |
|---|---|---|
| EP | 0 402 743 | 12/1990 |
| EP | 0 495 339 | 7/1992 |
| EP | 0 597 806 | 5/1994 |
| EP | 1 270 633 | 1/2003 |
| JP | 2000 143769 | 5/2000 |
| WO | 2005 061105 | 7/2005 |

* cited by examiner

*Primary Examiner* — Peter F Godenschwager
*Assistant Examiner* — David Karst
(74) *Attorney, Agent, or Firm* — Oblon, Spivak, McClelland, Maier & Neustadt, L.L.P.

(57) ABSTRACT

The preparation of epoxy resin compositions which comprise glycidyl ethers comprising cyclohexyl groups and have a low oligomer content is carried out by distillation of compositions which are obtainable by ring hydrogenation of compounds of the general formula (I)

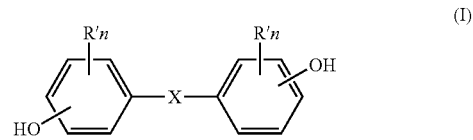

Figure 1A:
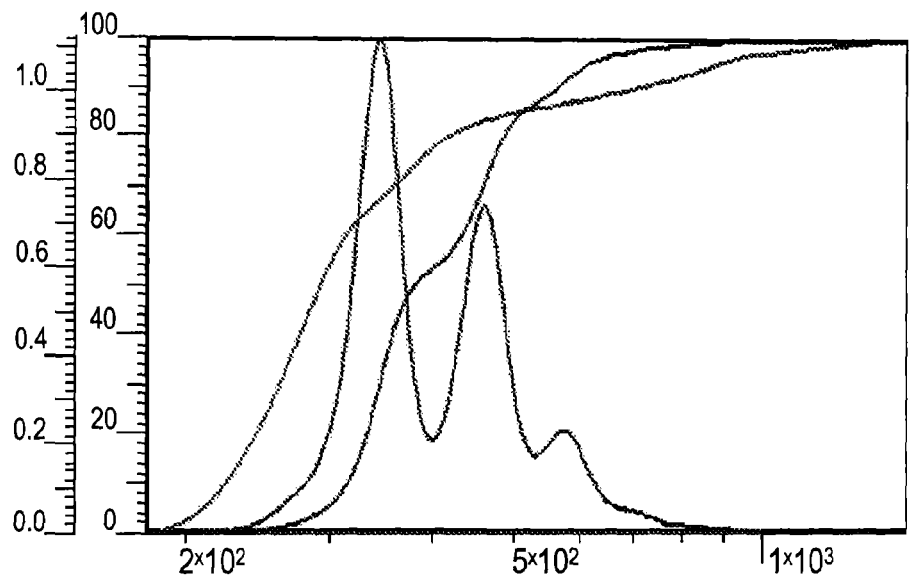

where
—X— is —$CR_2$—, —CO—, —O—, —S—, —$SO_2$—,
the radicals R are each, independently of one another, H, $C_{1-6}$-alkyl, $C_{3-6}$-cycloalkyl, in which one or more H atoms can be replaced by halogen,
the radicals R' are each, independently of one another, $C_{1-4}$-alkyl, halogen,
the indices n are each, independently of one another, 0, 1, 2 or 3,
and subsequent reaction of the hydroxyl groups with epichlorohydrin,
in thin film evaporators or short path evaporators at a temperature in the range from 150 to 270° C. and a pressure in the range from 0.001 to 1 mbar.

5 Claims, 2 Drawing Sheets

EPOXY RESIN COMPOSITIONS AND PROCESS FOR PREPARING THEM

The invention relates to a process for preparing epoxy resin compositions having a low oligomer content, epoxy resin compositions which can be obtained by the process and their use in, for example, light- and weathering-stable paints, varnishes and coatings or plastics and in the electronics industry as well as to LED's (light emitting diodes) or optical lenses prepared therewith.

Alicyclic epoxy resin compositions are used in many parts of the electronics industry as coating, encapsulation or sealing materials. Since the compositions have a low aromatics content, if any, they are frequently stable to light and yellowing. The epoxy resin compositions are frequently prepared from bisphenol A by reaction with epichlorohydrin and subsequent hydrogenation. Such processes are described, for example, in EP-A-1 270 633 and EP-A 0 402 743.

It is also possible for bisphenol A to be hydrogenated first and subsequently reacted with epichlorohydrin. Such a reaction is described, for example, in EP-A-0 597 806.

JP-A-2000-143769 likewise discloses a process for preparing an epoxy-comprising compound, in which hydrogenated bisphenol A is reacted with liquid epichlorohydrin in the presence of a quaternary ammonium salt and a solid alkali metal hydroxide at a temperature in the range from 20 to 70° C. while stirring.

While the products obtained by reaction of bisphenol A with epichlorohydrin and subsequent hydrogenation frequently meet the product purity requirements for electronics applications, this is not the case for the products prepared according to conventional processes by hydrogenation of bisphenol A and subsequent reaction with epichlorohydrin. However, the preparation of the epoxy resin compositions by the first process is significantly more expensive than by the latter process.

It is an object of the present invention to provide an economical process for preparing epoxy resin compositions which comprise glycidyl ethers comprising cyclohexyl groups and have the properties necessary for electronics applications. Especially for the production of LEDs, the epoxy resin compositions should be colorless, comprise very little or no (free) chlorine and have a low viscosity and also a low content of by-products.

According to the invention, the object is achieved by a process for preparing epoxy resin compositions which comprise glycidyl ethers comprising cyclohexyl groups and have a low oligomer content by distillation of compositions which are obtainable by ring hydrogenation of compounds of the general formula (I)

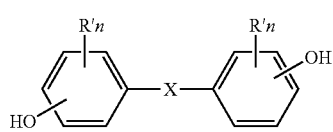

where
—X— is —CR$_2$—, —CO—, —O—, —S—, —SO$_2$—,
the radicals R are each, independently of one another, H, C$_{1-6}$-alkyl, C$_{3-6}$-cycloalkyl, in which one or more H atoms can be replaced by halogen,
the radicals R' are each, independently of one another, C$_{1-4}$-alkyl, halogen,
the indices n are each, independently of one another, 0, 1, 2 or 3,
and subsequent reaction of the hydroxyl groups with epichlorohydrin,
in thin film evaporators or short path evaporators at a temperature in the range from 150 to 270° C. and a pressure in the range from 0.001 to 1 mbar.

The object is also achieved by an epoxy resin composition which has a low oligomer content and can be obtained by the above process.

The object is also achieved by an epoxy resin composition which has a low oligomer content and is based on compounds of the general formula (II)

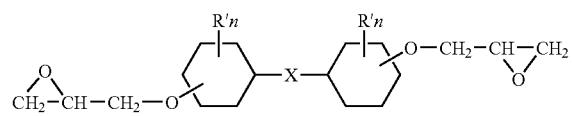

where
—X— is —CR$_2$—, —CO—, —O—, —S—, —SO$_2$—,
the radicals R are each, independently of one another, H, C$_{1-6}$-alkyl, C$_{3-6}$-cycloalkyl, in which one or more H atoms can be replaced by halogen,
the radicals R' are each, independently of one another, C$_{1-4}$-alkyl, halogen,
the indices n are each, independently of one another, 0, 1, 2 or 3,
wherein
the proportion of compounds having a molecular weight which is from 0.5 to 1.12 times the molecular weight of the compound of the general formula (II) is at least 60% by weight,
the proportion of compounds having a molecular weight which is from 1.12 to 1.53 times the molecular weight of the compound of the general formula (II) is less than 30% by weight and
the proportion of compounds having a molecular weight which is from 1.53 to 2.53 times the molecular weight of the compound of the general formula (II) is less than 2.5% by weight,
based on the total weight of the composition and determined by gel permeation chromatography.

The invention also provides for the use of the epoxy resin compositions in coating, encapsulation and sealing materials for the electronics industry and LEDs and optical lenses prepared therewith.

It has been found, according to the invention, that the reaction product from the ring hydrogenation of bisphenol A and subsequent reaction with epichlorohydrin can be purified by distillation in thin film evaporators or short path evaporators to such an extent that it is suitable for electronics applications. It has hitherto been considered that distillation of the reaction product with epichlorohydrin could not be carried out. In particular, it has not been believed, owing to the thermal stress in the distillation, that a product which has very good purity and a low chlorine content and meets the requirements for electronics applications can be obtained.

According to the invention, the distillation is carried out in thin film evaporators or short path evaporators. In both cases, a thin film distillation in which a considerable reduction in the boiling temperature is achieved by reducing the working pressure is carried out. In the case of a thin film evaporator, the crude product is preferably heated on the interior surface of an externally heated tube until the relatively low-boiling component begins to evaporate. The vapors are subsequently condensed in a condenser. In the case of a simple thin film evaporator, this condenser is positioned very close to the evaporator, while in the case of a short path evaporator it may even be located within the outer wall of the evaporator. Customary thin film evaporators can be operated at a minimum pressure of about 1 mbar, while short path evaporators are operated at a minimum pressure of about 0.001 mbar.

In thin film or short path evaporators, the residence time is very short. It is frequently only a few seconds.

In the case of a thin film evaporator, the product to be vaporized runs downward on the interior surface of an externally heated cylindrical tube. The liquid film is continually mixed by means of a wiper system so as to achieve homogeneity in the mixture to be vaporized. The condensation of the distillate is effected in an external condenser to which the vacuum system is connected. The thin film evaporator is typically supplied from the top with product which runs downward on the interior wall and is agitated by the wiper. The distillate is taken off at the top and condensed in the condenser. The distillation residue is taken off at the bottom of the thin film evaporator. The structural design with a connecting line between evaporator and condenser limits the reduced pressure which can be achieved to about 1 mbar.

Short path distillation allows the distillation to be carried out at very low temperatures and a short residence time. As in the case of a thin film evaporator, the short path distillation is a continuous process under reduced pressure.

Here too, vaporization occurs from a heated wiped film. The minimum pressure in the short path evaporator, which is significantly lower than that in a thin film evaporator, is achieved as a result of the vapors having to cover only a very short distance to reach an internal condenser. At the same time, the flow cross section for the vapors is as large as the evaporator surface. As a result, there is only a small pressure drop between evaporator surface and condenser. The typical pressure range for the short path distillation is a "high vacuum", i.e. from about 0.001 to 1 mbar. The temperature required can therefore be reduced to such an extent that no thermal damage to the products occurs at the short residence time.

As a result of the condenser being arranged within the evaporator, the vapor tube as connecting line between evaporator and condenser is dispensed with. At the low pressures which can be used, the vapors have a very large volume which leads to very high velocities even at large cross sections. This limits, for example, the pressure range of thin film evaporators.

In the case of the short path distillation, the evaporation preferably occurs from a thin film in the interior of a cylindrical tube, with the evaporator wall being heated from the outside by means of a double wall. The film is continually mixed by means of a wiper system so that a radial concentration gradient is largely avoided. The condenser is located within the evaporator. As a result, the path which the vapors have to cover is extremely short. If the distance between evaporator and condenser is in the order of magnitude of the average free path length of the molecules, the distillation is also referred to as molecular distillation. The average free path length in the gas space is frequently in the cm range. According to the invention, a molecular distillation of this type is preferably carried out. Molecular distillation can also be defined as short path distillation in vacuo or under reduced pressure.

Suitable thin film evaporators and short path evaporators can be obtained industrially. For example, suitable thin film evaporators and short path evaporators can be procured from VTA, Verfahrenstechnische Anlagen GmbH, D-94469 Deggendorf.

According to the invention, the distillation is carried out at a temperature in the range from 150 to 270° C. and a pressure in the range from 0.001 to 1 mbar. In one embodiment, the temperature can be in the range from 160 to 250° C.

Preference is given to carrying out a short path distillation or molecular distillation in which the pressure is from 0.003 to 0.3 mbar, in particular from 0.005 to 0.2 mbar.

In a preferred embodiment, the distillation is carried out at a temperature in the range from 150 to 230° C., preferably from 170 to 210° C., and a pressure in the range form 0.005 to 0.2 mbar, in particular from 0.007 to 0.1 mbar. Particularly advantageous products can be obtained at temperatures below 200° C., in particular below 190° C.

The physical design of the thin film evaporator or short path evaporator for evaporation of the compositions used according to the invention is known to those skilled in the art.

The process of the invention allows the preparation of epoxy resin compositions which comprise glycidyl ethers comprising cyclohexyl groups and have a low oligomer content. The epoxy resin compositions of the invention preferably have a very low aromatics content or comprise no remaining aromatics. The maximum amount of aromatic compounds, based on the epoxy resin compositions, is preferably 5% by weight, in particular 3% by weight. The compositions are particularly preferably aromatics-free.

The chlorine content of the compositions can be decreased greatly by the distillation according to the invention. The epoxy resin compositions obtained after hydrogenation of bisphenol A and subsequent reaction with epichlorohydrin usually comprise about 5% by weight of total chlorine, excluding halogen substituents on the bisphenol. The dynamic viscosity at 25° C. is above 2000 mPas, generally above 2200 mPas. The color number (Apha) is usually in the range from 22 to 28.

The process of the invention enables the dynamic viscosity to be reduced to less than 2000 mPas, preferably to less than 1200 mPas (at 25° C.). The chlorine content (total chlorine) can be reduced to low values of not more than 3% by weight, preferably 2.5% by weight and less, in particular 1.5% by weight and less. For example, the chlorine content can be reduced from 4.9% by weight to 1.3% by weight. The total chlorine content is determined by the Schoeniger method and does not include possible halogen substituents in R and R', although these are preferably not present.

The dynamic viscosity can preferably be reduced to from 1000 to 1300 mPas, in particular from 1100 to 1200 mPas. The short path evaporation thus leads to distillates having a lower viscosity and a lower chlorine content.

In the distillation according to the invention, the proportion of distillate is preferably from 25 to 90% by weight, particularly preferably from 40 to 90% by weight, in particular from 55 to 86% by weight. The proportion of distillate can be set by appropriate operation of the short path evaporator or thin film evaporator.

In the process of the invention, compositions which are obtainable by ring hydrogenation of compounds of the general formula (I)

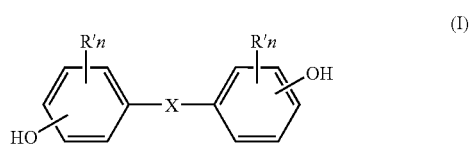

where
—X— is —CR$_2$—, —CO—, —O—, —S—, —SO$_2$—,
the radicals R are each, independently of one another, H, C$_{1-6}$-alkyl, C$_{3-6}$-cycloalkyl, in which one or more H atoms can be replaced by halogen,
the radicals R' are each, independently of one another, C$_{1-4}$-alkyl, halogen,
the indices n are each, independently of one another, 0, 1, 2 or 3,
and subsequent reaction of the hydroxyl groups with epichlorohydrin, are distilled.

The compound of the general formula (I) is preferably selected from among compounds in which —X— is —CR$_2$—, —CO— or —O—. R is preferably H or C$_{1-3}$-alkyl in which one or more H atoms can be replaced by halogen. Halogen is preferably fluorine, n is preferably 0, and halogen in R' is fluorine.

In the compound of the general formula (I) particular preference is given to X being —CH$_2$—, —C(CH$_3$)$_2$—, —C(CF$_3$)$_2$—, —CO— or —O—, n being 0 and the hydroxyl groups being in the p position relative to one another. Compounds of the general formula (I) which are particularly preferably used are bisphenol A and bisphenol F.

The hydrogenation of the compounds can be carried out by known methods. For suitable processes and catalysts, reference may be made, for example, to JP-A-2000-143769 and EP-A-0 597 806. Suitable catalysts are also described in EP-A-0 402 743, EP-A-1 270 633, U.S. Pat. No. 6,060,611, EP-A-0 814 098. Other suitable hydrogenation catalysts are described in U.S. Pat. No. 5,530,147, JP-A-2003-12659, U.S. Pat. No. 6,756,453, WO 2004/009526, JP-A-2002-249488, JP-A-2002-338559, JP-A-2002-338561 and WO 03/103830. For typical basic structures of the glycidyl ethers comprising cyclohexyl groups, reference may be made to EP-A-1 270 633, EP-A-0 597 806 and JP-A-2000-143769. It should be noted that the product composition for the hydrogenation of bisphenol A and subsequent reaction with epichlorohydrin is different from that for reaction of bisphenol A with epichlorohydrin and subsequent distillation. Epoxy resins obtained by hydrogenation of bisphenol A and subsequent reaction with epichlorohydrin are obtainable, for example, from Leuna Harze under the trade name Epilox®P2200. Similar products can be obtained from Hexion under the trade name Eponex®1510. The product Eponex 1510 from Hexion has, for example, an epoxide equivalent value of 213 g/eq., a total chlorine content of 4.9%, a color number of 23 Apha, a dynamic viscosity at 25° C. of 2290 mPas, a kinematic viscosity at 25° C. of 2100 mm$^2$/s and a density at 25° C. of 1.090 g/ml.

This starting mixture is, according to the invention, distilled so that the proportion of distillate is from 25 to 90% by weight, preferably from 55 to 86% by weight. An industrial process is, in particular, carried out at temperatures of from 207 to 240° C. and a pressure of from 0.02 to 0.13 mbar. This makes it possible to reduce the chlorine content from 4.9% to 1.3% and to reduce the dynamic viscosity from 2290 mPas to 1100-1200 mPas.

The distillates comprise, in particular, a significantly lower proportion of oligomers than the starting mixtures.

They are colorless, comprise little or no chlorine, display a low viscosity and have a low proportion of by-products. They can therefore be used particularly advantageously in coating, encapsulation and sealing materials for the electronics industry. They can particularly preferably be used for the encapsulation of LEDs. Such applications are also described, for example, in JP-A-2000-143769, EP-A-0 597 806 and in particular EP-A-1 270 633 and U.S. Pat. No. 6,060,611. Owing to the low viscosity, they can be processed particularly well in these applications, so that bubble-free and complete coatings and encapsulations are possible. The transparency, in particular their colorless nature, make them very suitable for optical applications. The very low chlorine content reliably reduces oxidation of metallic components.

The invention also provides the epoxy resin compositions having a low oligomer content which can be obtained by the above process. These compositions will be described in more detail below. The epoxy resin compositions are prepared by sequential hydrogenation of the bisphenol compounds, subsequent reaction of the hydroxyl groups with epichlorohydrin and subsequent short path distillation.

The epoxy resin compositions according to the invention are preferably compositions from a process for preparing epoxy resin compositions which comprise glycidyl ethers comprising cyclohexyl groups and have a low oligomer content by distillation of compositions which can be obtained by hydrogenation of compounds of the general formula (I) and subsequent reaction of the hydroxyl groups with epichlorohydrin and subsequent short path evaporation.

The proportion of compounds having from 0.5 to 1.12 times the molecular weight is preferably at least 70% by weight, in particular at least 80% by weight, while the proportion of compounds having from 1.12 to 1.53 times the molecular weight is preferably less than 20% by weight, preferably less than 15% by weight. The proportion of compounds having a molecular weight which is from 1.53 to 2.53 times the molecular weight of the compound of the general formula (II) is preferably less than 1.5% by weight, in particular less than 0.5% by weight. These values apply particularly at a wall temperature of from 170 to 210° C. and a pressure of from 0.007 to 0.01 mbar. In the case of a reaction on an industrial scale at wall temperatures of from 207 to 238° C. and a pressure in the range from 0.03 to 0.11 mbar, the proportion of compounds having a molecular weight which is from 0.5 to 1.12 times the molecular weight of the compound of the general formula (II) is particularly preferably at least 70% by weight, the proportion of compounds having a molecular weight which is from 1.12 to 1.53 times the molecular weight of the compound of the general formula (II) is preferably less than 26% by weight and the proportion of compounds which have a molecular weight of from 1.53 to 2.53 times the molecular weight of the compound of the general formula (II) is less than 2.3% by weight.

In the case of the bisglycidyl ether of hydrogenated bisphenol A having a molecular weight of 340 g/mol, the corresponding ranges are from 180 to 380 g/mol, from 380 to 520 g/mol and from 520 to 860 g/mol.

The weight distribution of the composition is determined by gel permeation chromatography. The determination is carried out under the following conditions:

GPC Measurement Conditions

| | |
|---|---|
| Stationary phase: | 5 styrene-divinylbenzene gel columns PSS SDV [1 × E2 Å//3 × E4 Å//1E5 Å] (each 300 × 8 mm) from PSS GmbH (temperature: 35° C.) |
| Mobile phase: | THF (flow: 1.2 ml/min) |
| Calibration: | MW 500-5 000 000 g/mol using PS calibration kit from Polymer Laboratories In the oligomer range: ethylbenzene/1,3-diphenylbutane/1,3,5-tri-phenylhexane/1,3,5,7-tetraphenyloctane/1,3,5,7,9-pentaphenyl-decane Evaluation limit: 180 g/mol |
| Detection: | RI (refractive index) Waters 410 UV (at 254 nm) Spectra Series UV 100 |

The mixture used for the distillation, for example Eponex® 1510, displays two strong peaks in the GPC curve in the range from 400 to 500 g/mol and in the range from 520 to 700 g/mol. After the distillation, the peak in the range from 520 to 700 g/mol is significantly smaller, frequently not more than one third of the height of the peak in the range from 400 to 500 g/mol. In return, a significantly larger peak in the range from 300 to 400 g/mol is obtained.

Figure 1B:
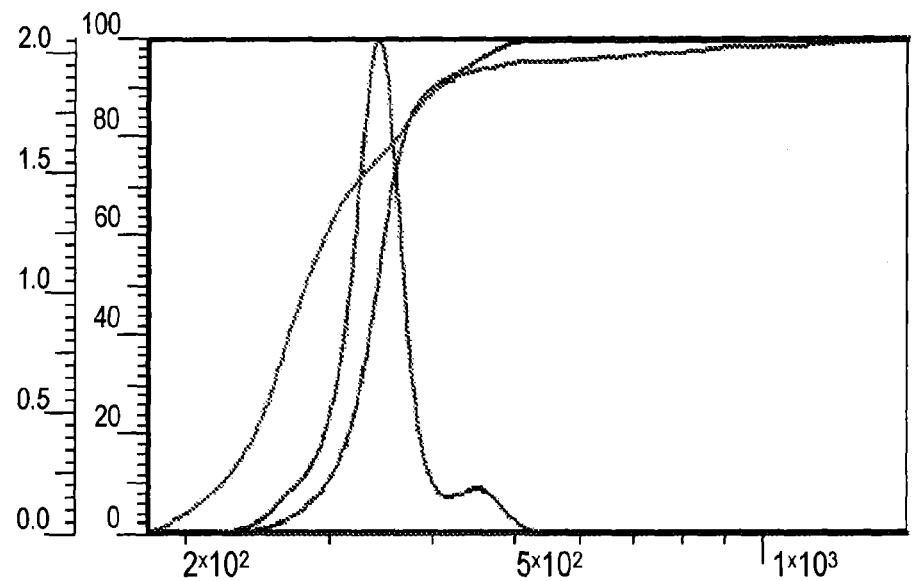
Figure 1C:
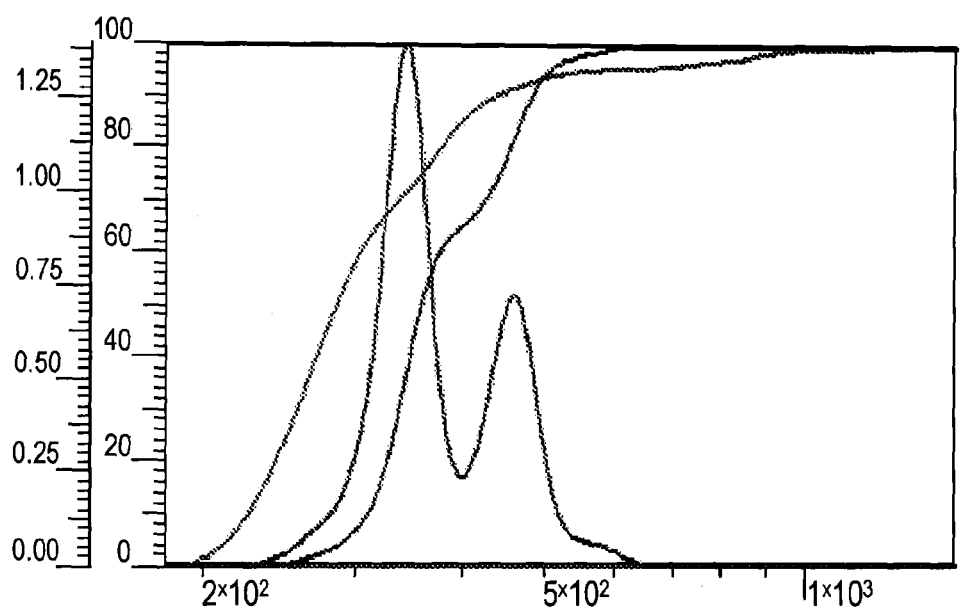

FIG. 1 shows GPC distributions for the starting material (a) and two distillates (b, c).

The main difference between the product after the distillation and the product before the distillation is that the pronounced peak in the range from 520 to 700 g/mol has become a small shoulder and thus no longer an individual peak.

While the main products are the same, the by-product spectrum is altered. The specific by-products effectively represent a fingerprint of the process and the products differ from the products obtained by previous processes, in particular products obtained by initial reaction with epichlorohydrin and subsequent hydrogenation. The advantageous property spectrum makes the compositions of the invention suitable for all applications in surface coatings and in the electronics industry, for example coating, encapsulation, casting or sealing compositions. The compositions are light-stable, in particular UV-stable, and do not tend to undergo yellowing and have little or no intrinsic color. The invention also relates to a LED having a sealing or encapsulation material, that contains or consists of an epoxy resin composition as described above, which can optionally be cured. The invention also relates to optical lenses made from this material.

The invention is illustrated by the following examples.

EXAMPLE 1

The hydrogenated bisglycidyl ether Eponex® 1510 from Hexion, which is based on hydrogenated bisphenol A, was used as starting material. The distillation was carried out as a short path distillation or molecular distillation at temperatures in the range from 170 to 210° C. and pressures in the range from 0.007 to 0.01 mbar.

At a wall temperature of 170° C. and a pressure of 0.01 mbar and a proportion of distillate of 53.2%, the proportion of product in the range from 180 to 380 g/mol was increased from 50.42% to 86.62%, while that in the range from 380 to 520 g/mol was reduced from 35.65% to 13.01%, that in the range from 520 to 860 g/mol was reduced from 13.15% to 0.38% and that in the range from 860 to 1500 g/mol was reduced from 0.74 to 0.02%.

The following specific results were obtained (GPC analysis as described above):

The invention claimed is:
1. A process,
comprising distilling an epoxy resin composition which comprises a glycidyl ether comprising a cyclohexyl group and having a low oligomer content wherein said composition is prepared by ring hydrogenation of a compound of general formula (I)

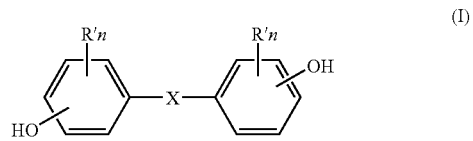

(I)

wherein
—X— is —CR$_2$—, —CO—, —O—, —S—, or —SO$_2$—,
the radicals R are each, independently of one another, H, C$_{1-6}$-alkyl, or C$_{3-6}$-cycloalkyl, wherein one or more H atoms can be replaced by halogen,
the radicals R' are each, independently of one another, C$_{1-4}$-alkyl, or halogen, and
the indices n are each, independently of one another, 0, 1, 2 or 3,
and said composition is further prepared by subsequent reaction of the hydroxyl groups with epichlorohydrin,
wherein said distillation is carried out in a short path evaporator at a temperature in the range from 150 to 230° C. under a pressure in the range from 0.005 to 0.2 mbar,
wherein the distilling forms an epoxy resin composition containing not more than 2.5% by weight of chlorine, and wherein the epoxy resin composition has a low oligomer content and comprises one or more compounds of formula (II):

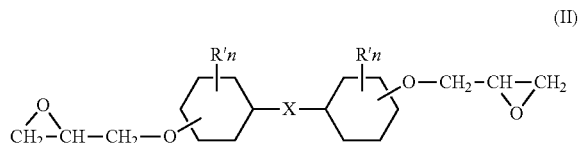

(II)

wherein —X— is —CR$_2$—, —CO—, —O—, —S—, or —SO$_2$—;
the radicals R are each, independently of one another, H, C$_{1-6}$-alkyl or C$_{3-6}$-cycloalkyl, wherein one or more H atoms can be replaced by halogen;
the radicals R' are each, independently of one another, C$_{1-4}$-alkyl, or halogen;

| | Wall temp. [° C.] | Feed Pressure [mbar] | rate [g/h] | Ratio of distillate/ residue [%] | Color number [Apha] | EEW [g/eq] | Total chlorine [%] | Dyn. viscosity 25° C. mPa*s | Kin. viscosity 25° C. mm$^2$/s | Kin. viscosity 25° C. mm$^2$/s | GPC (g/mol) | | | |
|---|---|---|---|---|---|---|---|---|---|---|---|---|---|---|
| | | | | | | | | | | | 180-380 % rel. | 380-520 % rel. | 520-860 % rel. | 860-1500 % rel. |
| Feed | | | | | 23-28 | 213 | 4.9 | 2290 | 2100 | 2100 | 50.42 | 35.65 | 13.15 | 0.74 |
| Distillate | 170 | 0.01 | 633 | 46.8 | | 197 | 1.3 | 1130 | 1060 | 1060 | 86.62 | 13.01 | 0.38 | 0.02 |
| Distillate | 200 | 0.007 | 467 | 16.6 | 13 | 204 | 3.3 | 1770 | 1640 | | 61.53 | 35.06 | 3.37 | 0.03 |

At a higher distillation temperature, total chlorine and viscosity increase. FIG. 1 shows the molar mass distributions (D) for the starting material (a), the distillate at 170° C. (b) and the distillate at 200° C. (c). As integral, rel. W (log M) [ ] is reported.

n are each, independently of one another, 0, 1, 2 or 3; and
wherein the proportion of compounds having a molecular weight of from 0.5 to 1.12 times the molecular weight of the compound of the general formula (II) is at least 60% by weight;

the proportion of compounds having a molecular weight of from greater than 1.12 to 1.53 times the molecular weight of the compound of the general formula (II) is less than 30% by weight; and the proportion of compounds having a molecular weight of from greater than 1.53 to 2.53 times the molecular weight of the compound of the general formula (II) is less than 2.5% by weight.

2. A process, comprising distilling an epoxy resin composition which comprises a glycidyl ether comprising a cyclohexyl group and having a low oligomer content wherein said composition is prepared by ring hydrogenation of a compound of general formula (I)

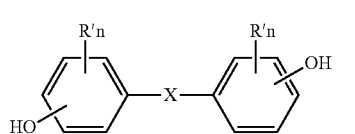

(I)

wherein

—X— is —$CR_2$—, —CO—, —O—, —S—, or —$SO_2$—, the radicals R are each, independently of one another, H, $C_{1-6}$-alkyl, or $C_{3-6}$-cycloalkyl, wherein one or more H atoms can be replaced by halogen, the radicals R' are each, independently of one another, $C_{1-4}$-alkyl, or halogen, and the indices n are each, independently of one another, 0, 1, 2 or 3, and said composition is further prepared by subsequent reaction of the hydroxyl groups with epichlorohydrin, wherein said distillation is carried out in a short path evaporator at a temperature in the range from 150 to 230° C. under a pressure in the range from 0.005 to 0.2 mbar, wherein the distilling forms an epoxy resin composition containing not more than 2.5% by weight of chlorine, wherein the epoxy resin composition has a low oligomer content and comprises one or more compounds of formula (II):

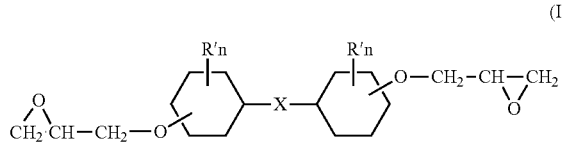

(II)

wherein —X— is —$CR_2$—, —CO—, —O—, —S—, or —$SO_2$—;

the radicals R are each, independently of one another, H, $C_{1-6}$-alkyl or $C_{3-6}$-cycloalkyl, wherein one or more H atoms can be replaced by halogen;

the radicals R' are each, independently of one another, $C_{1-4}$-alkyl, or halogen;

n are each, independently of one another, 0, 1, 2 or 3; and wherein the proportion of compounds having a molecular weight of from 0.5 to 1.12 times the molecular weight of the compound of the general formula (II) is at least 60% by weight;

wherein the proportion of compounds having a molecular weight of from greater than 1.12 to 1.53 times the molecular weight of the compound of the general formula (II) is less than 30% by weight;

wherein the proportion of compounds having a molecular weight of from greater than 1.53 to 2.53 times the molecular weight of the compound of the general formula (II) is less than 2.5% by weight, and wherein the low oligomer epoxy resin composition comprises at least 80% by weight of compounds having a molecular weight of from 0.5 to 1.12 times the molecular weight of the compound of formula (II).

3. A process, comprising distilling an epoxy resin composition which comprises a glycidyl ether comprising a cyclohexyl group and having a low oligomer content wherein said composition is prepared by ring hydrogenation of a compound of general formula (I)

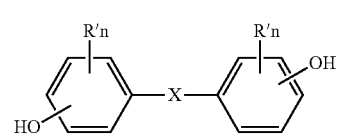

(I)

wherein

—X— is —$CR_2$—, —CO—, —O—, —S—, or —$SO_2$—, the radicals R are each, independently of one another, H, $C_{1-6}$-alkyl, or $C_{3-6}$-cycloalkyl, wherein one or more H atoms can be replaced by halogen, the radicals R' are each, independently of one another, $C_{1-4}$-alkyl, or halogen, and the indices n are each, independently of one another, 0, 1, 2 or 3, and said composition is further prepared by subsequent reaction of the hydroxyl groups with epichlorohydrin, wherein said distillation is carried out in a short path evaporator at a temperature in the range from 150 to 230° C. under a pressure in the range from 0.005 to 0.2 mbar, wherein the distilling forms an epoxy resin composition containing not more than 2.5% by weight of chlorine, and wherein the epoxy resin composition has a low oligomer content and comprises one or more compounds of formula (II):

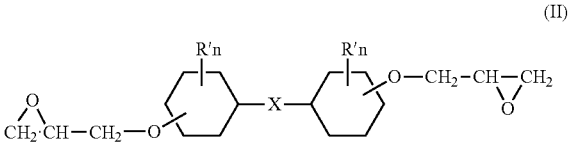

(II)

wherein —X— is —$CR_2$—, —CO—, —O—, —S—, or —$SO_2$—;

the radicals R are each, independently of one another, H, $C_{1-6}$-alkyl or $C_{3-6}$-cycloalkyl, wherein one or more H atoms can be replaced by halogen;

the radicals R' are each, independently of one another, $C_{1-4}$-alkyl, or halogen;

n are each, independently of one another, 0, 1, 2 or 3; and wherein the proportion of compounds having a molecular weight of from 0.5 to 1.12 times the molecular weight of the compound of the general formula (II) is at least 60% by weight;

wherein the proportion of compounds having a molecular weight of from greater than 1.12 to 1.53 times the molecular weight of the compound of the general formula (II) is less than 30% by weight;

wherein the proportion of compounds having a molecular weight of from greater than 1.53 to 2.53 times the molecular weight of the compound of the general formula (II) is less than 2.5% by weight, and wherein the low oligomer epoxy resin composition comprises 0.5% by weight or less of compounds having a molecular weight of from greater than 1.53 to 2.53 times the molecular weight of the compound of formula (II).

4. A process, comprising distilling an epoxy resin composition which comprises a glycidyl ether comprising a cyclohexyl group and having a low oligomer content wherein said composition is prepared by ring hydrogenation of a compound of general formula (I)

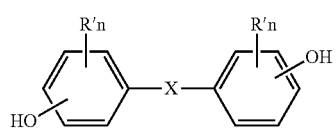

(I)

wherein

—X— is —CR$_2$—, —CO—, —O—, —S—, or —SO$_2$—, the radicals R are each, independently of one another, H, C$_{1-6}$-alkyl, or C$_{3-6}$-cyclo-alkyl, wherein one or more H atoms can be replaced by halogen, the radicals R' are each, independently of one another, C$_{1-4}$-alkyl, or halogen, and the indices n are each, independently of one another, 0, 1, 2 or 3, and said composition is further prepared by subsequent reaction of the hydroxyl groups with epichlorohydrin, wherein said distillation is carried out in a short path evaporator at a temperature in the range from 150 to 230° C. under a pressure in the range from 0.005 to 0.2 mbar, wherein the distilling forms an epoxy resin composition containing not more than 2.5% by weight of chlorine, and wherein the epoxy resin composition has a low oligomer content and comprises one or more compounds of formula (II):

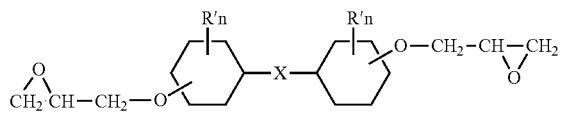

(II)

wherein —X— is —CR$_2$—, —CO—, —O, —S—, or —SO$_2$—;

the radicals R are each, independently of one another, H, C$_{1-6}$-alkyl or C$_{3-6}$-cycloalkyl, wherein one or more H atoms can be replaced by halogen;

the radicals R' are each, independently of one another, C$_{1-4}$-alkyl, or halogen;

n are each, independently of one another, 0, 1, 2 or 3; and wherein the proportion of compounds having a molecular weight of from 0.5 to 1.12 times the molecular weight of the compound of the general formula (II) is at least 60% by weight;

wherein the proportion of compounds having a molecular weight of from greater than 1.12 to 1.53 times the molecular weight of the compound of the general formula (II) is less than 30% by weight;

wherein the proportion of compounds having a molecular weight of from greater than 1.53 to 2.53 times the molecular weight of the compound of the general formula (II) is less than 2.5% by weight, and wherein the low oligomer epoxy resin composition comprises 1.5% by weight or less of compounds having a molecular weight of greater than 1.53 to 2.53 times the molecular weight of the compound of formula (II).

5. A process, comprising:

distilling a reaction mixture to obtain an epoxy resin composition;

wherein the reaction mixture is a reaction product of epichlorohydrin with a ring hydrogenation product of a compound of formula (I)

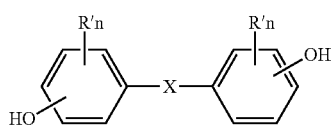

(I)

wherein —X— is —CR$_2$—, —CO—, —O, —S—, or —SO$_2$—;

the radicals R are each, independently of one another, H, C$_{1-6}$-alkyl, or C$_{3-6}$-cycloalkyl, wherein one or more H atoms can be replaced by halogen;

the radicals R' are each, independently of one another, C$_{1-4}$-alkyl, or halogen; and n are each, independently of one another, 0, 1, 2 or 3;

wherein the distilling is carried out in at least one of a short path evaporator and a thin film evaporator at a temperature of from 150-230° C. and under a pressure of from 0.005 to 0.2 mbar to form a low oligomer epoxy resin composition, wherein at least 80% by weight of the product formed by the distilling has a molecular weight of from 180 to 380 g/mol.

* * * * *